US012564682B2

(12) United States Patent
Du et al.

(10) Patent No.: US 12,564,682 B2
(45) Date of Patent: Mar. 3, 2026

(54) MEDICAL DELIVERY DEVICE AND DRUG DELIVERY SYSTEM

(71) Applicant: SHANGHAI MICROPORT MEDICAL (GROUP) CO., LTD., Shanghai (CN)

(72) Inventors: Qiran Du, Shanghai (CN); Meng Li, Shanghai (CN); Junfei Li, Shanghai (CN)

(73) Assignee: SHANGHAI MICROPORT MEDICAL (GROUP) CO., LTD., Shanghai (CN)

( * ) Notice: Subject to any disclaimer, the term of this patent is extended or adjusted under 35 U.S.C. 154(b) by 534 days.

(21) Appl. No.: 18/251,631

(22) PCT Filed: Oct. 28, 2021

(86) PCT No.: PCT/CN2021/127205
§ 371 (c)(1),
(2) Date: May 3, 2023

(87) PCT Pub. No.: WO2022/095791
PCT Pub. Date: May 12, 2022

(65) Prior Publication Data
US 2024/0009396 A1 Jan. 11, 2024

(30) Foreign Application Priority Data
Nov. 9, 2020 (CN) ......................... 202011241150.3

(51) Int. Cl.
*A61M 5/24* (2006.01)
*A61M 25/10* (2013.01)
(52) U.S. Cl.
CPC .......... *A61M 5/2448* (2013.01); *A61M 25/10* (2013.01); *A61M 2025/1086* (2013.01)

(58) Field of Classification Search
CPC ................ A61M 5/2448; A61M 25/10; A61M 2025/1086
See application file for complete search history.

(56) References Cited

U.S. PATENT DOCUMENTS 4,171,698 A 10/1979 Genese
4,496,344 A 1/1985 Kamstra
(Continued)

FOREIGN PATENT DOCUMENTS

CN 103285454 A 9/2013
CN 104784786 A 7/2015
(Continued)

*Primary Examiner* — Dung T Ulsh
(74) *Attorney, Agent, or Firm* — MUNCY, GEISSLER, OLDS & LOWE, P.C.

(57) ABSTRACT

A drug delivery system includes a medical delivery device, a dispersed substance, a liquid dispersion medium and a balloon catheter. The medical delivery device includes a first housing member, a second housing member and a push mechanism. The first housing member defines a first storage chamber, and the second housing member is disposed over the first housing member and defines a second storage chamber. In a first operational configuration, the first storage chamber is not in communication with the second storage chamber. In a second operational configuration, the first storage chamber is in communication with the second storage chamber, allowing the liquid dispersion medium in the first storage chamber to enter the second storage chamber to be mixed with the dispersed substance to produce a dispersion system. In a third operational configuration, the push mechanism drives the first housing member to move relative to the second housing member.

10 Claims, 9 Drawing Sheets

(56)         References Cited

U.S. PATENT DOCUMENTS

| | | | | |
|---|---|---|---|---|
| 5,484,411 | A | * | 1/1996 | Inderbitzen ......... A61M 25/104 |
| | | | | 604/103.08 |
| 5,562,620 | A | * | 10/1996 | Klein .................. A61M 25/104 |
| | | | | 604/509 |
| 2009/0131864 | A1 | | 5/2009 | Pickhard |
| 2016/0296703 | A1 | | 10/2016 | Bailey et al. |
| 2017/0368226 | A1 | * | 12/2017 | Pilkington ........ A61M 5/31513 |

FOREIGN PATENT DOCUMENTS

| | | | |
|---|---|---|---|
| CN | 206482927 | U | 9/2017 |
| CN | 111298274 | A | 6/2020 |
| CN | 211158062 | U | 8/2020 |
| CN | 112245784 | A | 1/2021 |
| CN | 214485280 | U | 10/2021 |
| GB | 1130593 | A | 10/1968 |

* cited by examiner

272

27

273

27

292

291

291

295

296

MEDICAL DELIVERY DEVICE AND DRUG DELIVERY SYSTEM

TECHNICAL FIELD

The present invention relates to the field of medical instruments and, in particular, to a medical delivery device and drug delivery system.

BACKGROUND

In recent years, cardiovascular disease has become a major human health threat. Among cardiovascular diseases, coronary artery disease is very common, and its incidence is increasing year by year. In 2018, more than 900,000 coronary interventional procedures were conducted in China, with an increase of about 21.5% year-on-year. The compound growth rate from 2009 to 2018 is 16.7%, showing an overall trend of accelerated growth. Among coronary interventional procedures, treatment of coronary artery stenosis with implanted stents is dominant. According to disclosed data, stenting procedures accounts for nearly 90%, and as many as more than one million stents are implanted in each single year. However, there is growing comprehensive assessment evidence that drug-coated balloons (DCBs) are more favorable in some cases. As a new interventional technique, a DCB is a balloon coated on its surface with a drug that inhibits cell proliferation, which is designed to be dilated to deliver the drug into the wall of a blood vessel at a lesion site therein, thus enabling it to provide an effect of inhibiting the proliferation of smooth muscle. However, in clinical applications, DCBs have been found with significant drug loss during delivery and dilation—about 10% to 25% of the coated drug is lost during advancement of the balloon through blood vessels; about 1% to 10% is virtually transferred to target tissue; about 60% to 70% escapes into the distal circulation after dilation; and 10% to 20% remains on the dilated balloon. Therefore, for DCBs, how to reduce the significant drug loss during delivery and how to increase the efficiency of drug transfer into tissue remains as problems in need of solving.

Drug infusion balloons are a potential alternative to DCBs. When a drug infusion balloon reaches a target site in a blood vessel, a drug fluid is pressurized with a dilator so that it passes through a balloon catheter into a balloon and flows out of the balloon through pores therein. This design can solve the problem of significant drug loss during delivery arising from the use of DCBs. Moreover, the drug fluid is directly output, dispensing with the need for waiting for the dissolution of a drug coating as is necessary when a DCB is used. Thus, it effectively increases the efficiency of drug transfer into tissue.

However, drug infusion balloons are disadvantageous in that storage of the drug fluid to be infused requires additional design. Typically, the drug fluid to be infused is stored in the form of a dry powder, because when it is stored as a fluid, aggregation of drug particles may occur therein, leading to a shorter shelf life. However, in doing so, it is necessary to add a chamber for storing the drug powder, and the drug fluid must be prepared from the drug powder in a suspension chamber before it can be pressurized by the dilator to flow out. Transferring the drug across so many chambers would increase the complexity of clinical surgery and is associated with a risk of drug fluid contamination.

SUMMARY OF THE INVENTION

It is an object of the present invention to provide a medical delivery device and a drug delivery system, which are improved compared with existing drug infusion balloons because they involve less complicated operation and fewer transfers of a drug fluid across different chambers, allow more convenient operation and storage, and reduce a risk of the drug fluid being contaminated during such transfers.

The above and other related objects are attained by a medical delivery device provided in the present invention, which comprises:

a housing comprising a first housing member and a second housing member, the first housing member defining a first storage chamber for storing a liquid dispersion medium therein, the second housing member disposed over the first housing member, the second housing member defining a second storage chamber for storing a dispersed substance therein, the second storage chamber having a delivery port for communicating with an external mechanism; and a push mechanism connected to the first housing member, the medical delivery device having a first operational configuration, a second operational configuration and a third operational configuration, wherein in the first operational configuration of the medical delivery device, the first storage chamber is not in communication with the second storage chamber;

in the second operational configuration of the medical delivery device, the first storage chamber is in communication with the second storage chamber, allowing the liquid dispersion medium to enter the second storage chamber to be mixed with the dispersed substance to produce a dispersion system; and in the third operational configuration of the medical delivery device, the push mechanism drives the first housing member to move relative to the second housing member, causing the dispersion system in the second storage chamber to flow through the delivery port into the external mechanism.

Optionally, the push mechanism may comprise a handle, a plunger and a pushrod, the handle connected to the first housing member and protruding out of the second housing member, the plunger disposed in the first housing member, the pushrod passed through the handle and connected to the plunger, wherein the first storage chamber is positioned between the plunger and the second storage chamber;

the pushrod is configured to be selectively locked to the handle;

when the pushrod is unlocked from the handle, and when the first storage chamber is brought into communication with the second storage chamber, the pushrod drives the plunger to move, causing the liquid dispersion medium to enter the second storage chamber and be mixed with the dispersed substance to produce the dispersion system; and when the pushrod is locked to the handle, the pushrod and the handle together drive the first housing member to move, causing the dispersion system in the second storage chamber to flow through the delivery port into the external mechanism.

Optionally, the medical delivery device may further comprise a locking mechanism for selectively locking the pushrod to the handle.

Optionally, the locking mechanism may comprise a locking projection and a locking recess, one of which is provided on the pushrod, and the other is provided on the handle.

Optionally, the locking recess may be provided on the pushrod and the locking projection on the handle, wherein the locking mechanism further comprises an openable and closable locking box serving as the locking projection, the locking box defined at a proximal end of the handle and comprising a slot and a bolt, wherein a plurality of locking recesses are spaced apart along a lengthwise direction of the pushrod; the pushrod is inserted in the slot; and the bolt is configured to be selectively locked in any one of the locking recesses on the pushrod; and/or wherein the handle defines a raised portion at the proximal end thereof, which is provided thereon with a locking post serving as the locking projection, and the locking recess is provided at a proximal end of the pushrod and configured to engage and cooperate with the locking post.

Optionally, the second housing member may have an internal thread, and the first housing member may have an external thread engageable with the internal thread.

Optionally, a spacer may be disposed between the first storage chamber and the second storage chamber, the spacer configured to be torn under the action of a force, thereby bringing the first storage chamber into communication with the second storage chamber.

Optionally, the spacer may be configured as a film structure which is configured to be torn under the action of a force, wherein the medical delivery device further comprises a piercing mechanism disposed between the spacer and the second storage chamber and configured to tear the film structure.

Optionally, the piercing mechanism may comprise a base and a piercing element arranged on the base, the base connected to the second housing member, the piercing element arranged on a side of the base facing the spacer, the piercing mechanism defining a channel allowing passage of the liquid dispersion medium therethrough, wherein the spacer defines the first storage chamber together with the first housing member and defines a nozzle chamber together with the piercing mechanism, or wherein the piercing mechanism and the first housing member together defines an accommodating chamber, which is divided by the spacer into the first storage chamber and a nozzle chamber.

Optionally, the base may be a solid baseplate, wherein the piercing element is a bored needle.

Alternatively, the base may be a ring, wherein the piercing element is made up of a number of blades arranged on the ring along circumference thereof.

Alternatively, the base may be an annular base, wherein the piercing element is a sawtooth bar which is connected at both ends to the annular base.

Optionally, the medical delivery device may further comprise a filtration membrane disposed in the second storage chamber so as to cover the delivery port.

Optionally, the medical delivery device may further comprise a monitoring mechanism for monitoring a pressure and/or a flow rate of the dispersion system.

The above and other related objects are also attained by a drug delivery system provided in the present invention, which comprises:

the medical delivery device as defined above;

a solid dispersed substance placed in the second storage chamber;

a liquid dispersion medium contained in the first storage chamber; and a balloon catheter comprising a catheter body and a balloon, the balloon disposed at a distal end of the catheter body and having micropores, the catheter body brought into communication at a proximal end thereof with the delivery port.

Compared with the prior art, the medical delivery device and the drug delivery system of the present invention combine preparation, storage and delivery of the dispersion system, allowing a dispersion system infusion process that is simpler than conventional processes. Moreover, they reduce transfers of the dispersion system among different chambers arranged outside of the device, thereby lowering a risk of the dispersion system being contaminated during such transfers. In other words, the dispersion system can be successively prepared and delivered within the medical delivery device, without introducing any additional container, thereby avoiding the dispersion system from being contaminated during delivery.

BRIEF DESCRIPTION OF THE DRAWINGS

Those of ordinary skill in the art would appreciate that the accompanying drawings are provided to facilitate a better understanding of the present invention and do not limit the scope thereof in any sense, in which.

Figure 1:
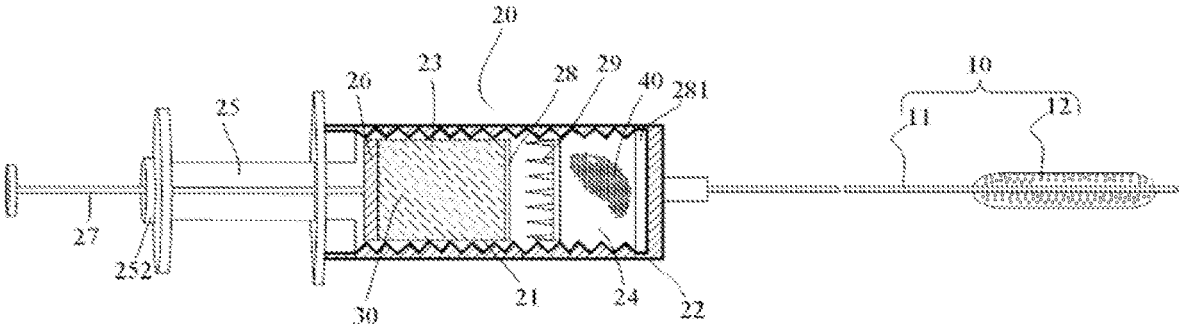
FIG. 1 is a schematic diagram showing the structure of a drug delivery system according to a preferred embodiment of the present invention, in which a piercing mechanism is implemented as bored needles.

In these figures,

10 denotes a balloon catheter; 11, a catheter body; 12, a balloon; 20, a medical delivery device; 21, a first housing member; 22, a second housing member; 23, a first storage chamber; 24, a second storage chamber; 25, a handle; 251, a first locking projection; 252, a locking box; 253, a slot; 254, a bolt; 255, a locking post; 256, a raised portion; 26, a plunger; 27, a pushrod; 271, a first locking recess; 272, a locking slot; 273, a third locking recess; 28, a spacer; 29, a piercing mechanism; 291, a bored needle; 292, a baseplate; 293, a blade; 294, a ring; 295, a sawtooth bar; 296, an annular base; 281, a filtration membrane; 30, a liquid dispersion medium; and 40, a dispersed substance.

Throughout the several views, like numerals indicate like elements.

DETAILED DESCRIPTION

Particular embodiments of the present invention will be described below by way of specific examples. Based on the disclosure and teachings provided herein, a person of ordinary skill in the art will readily realize other advantages and benefits provided by the present invention. The present invention may also be otherwise embodied or applied through different embodiments, and various modifications or changes may be made to the details disclosed herein from different points of view or for different applications, without departing from the spirit of the present invention. It should be noted that the accompanying drawings are provided herein merely to schematically illustrate the basic concept of the present invention. Accordingly, they only show components relating to the present invention but not necessarily depict all the components as well as their real shapes and dimensions in practical implementations. In practice, the configurations, counts and relative scales of the components may vary arbitrarily and their arrangements may be more complicated.

In the following, each of the embodiments is described as having one or more technical features. However, this does not mean that the present invention must be practiced necessarily with all such technical features, or separately with some or all the technical features in any of the embodiments. In other words, as long as the present invention can be put into practice, a person skilled in the art may choose some or all of the technical features in any of the embodiments or combine some or all of the technical features in different embodiments based on the teachings herein and depending on relevant design specifications or the requirements of practical applications. In this way, the present invention can be carried out more flexibly.

As used herein, the singular forms "a", "an" and "the" include plural referents, and the plural form "a plurality of" means "two or more", unless the context clearly dictates otherwise. As used herein, the term "distal" generally refers to an end that enters the body of a patient first, and the term "proximal" generally refers to an end opposite the "distal" end. As used herein, the term "or" is generally employed in the sense including "and/or" unless the context clearly dictates otherwise. It is to be also understood that the present disclosure may repeat reference numerals and/or letters in the various embodiments. This repetition is for the purpose of simplicity and clarity and does not in itself indicate a relationship between the various embodiments and/or configurations discussed herein. It is to be also understood that when an element is referred to as being "connected" to another element, it can be directly connected to the other element, or one or more intervening elements may be present.

In order to illustrate the embodiments of the present invention, a solid drug preparation is used as a suitable example of a dispersed substance.

FIG. 1 is a schematic diagram showing the structure of a drug delivery system according to a preferred embodiment of the present invention. As shown in FIG. 1, embodiments of the present invention provide a drug delivery system including a balloon catheter 10, a medical delivery device 20, a liquid dispersion medium 30 and a dispersed substance 40. The dispersed substance 40 is a solid drug preparation that can be dispersed in the liquid dispersion medium 30 to produce a liquid drug preparation.

The balloon catheter 10 includes a catheter body 11 and a balloon 12 disposed at a distal end of the catheter body 11. The balloon 12 has micropores (not shown) for release of a dispersion system (drug fluid). The present invention is not limited to any particular size, count or distribution pattern of the micropores in the balloon 12, and the "micropores" are pores with small diameters of, for example, several microns or several nanometers. Generally, the balloon 12 is made of an elastic material, which may be selected from Pebax, a block copolymer made up of polyether blocks and polyamide blocks, polyethylene, polyamide and the like. The balloon 12 may be an angioplasty balloon or another other balloon for intervention on a blood vessel. The micropores in the balloon 12 serve for release of a dispersion system, which then comes into contact with a target site in a blood vessel. The present invention is not limited to any particular formation method of the micropores, and suitable examples of the formation method may include laser perforation, perforation with a microliter syringe, and the like. The micropores may be distributed regularly or irregularly, and may have a diameter of 5 microns to 500 microns, preferably 10 microns to 250 microns, more preferably 10 microns to 50 microns. The number of the micropores may be 1 to 100, preferably 5 to 50.

The catheter body 11 is configured to be connected at a proximal end thereof to the medical delivery device 20. The present invention is not limited to how the medical delivery device 20 is connected to the proximal end of the balloon catheter 10. For example, they may be connected together detachably or undetachably. The medical delivery device 20 serves mainly for the preparation and storage of a dispersion system and delivery thereof to the balloon catheter 10.

A housing of the medical delivery device 20 includes a first housing member 21 and a second housing member 22. The first housing member 21 is disposed within the second housing member 22. The first housing member 21 defines a first storage chamber 23, and the second housing member 22 defines a second storage chamber 24. The first storage chamber 23 is configured for storage of the liquid dispersion medium 30. The liquid dispersion medium 30 may be any one or a liquid mixture of liquids such as purified water, a saline solution and a contrast medium, and other substances may be added thereto. The second storage chamber 24 is configured for storage of the dispersed substance 40. The dispersed substance 40 may be a pure drug, or a complex of a drug with a polymer, an excipient, a stabilizer, an adjuvant or the like. The polymer may be a polymeric material that facilitates sustained release or adsorption of the drug. The present invention is not limited to any particular polymeric material. In case of the dispersed substance 40 being a compound substance, the formation of a stable suspension, preferably a nano-drug suspension, in the liquid dispersion medium 30 can be facilitated. Particles in the suspension are preferred to have a particle size of 30 nm to 500 nm, more preferably 35 nm to 300 nm. It is to be noted that the present invention is not limited to how the dispersed substance 40 is stored in the second storage chamber 24. For example, it may be directly contained in the second storage chamber 24, or stored therein in the form of a coating on a wall of the second storage chamber 24. The dispersed substance 40 may be formulated as a powder, granules, tablets, capsules or another conventional formulation, or as microspheres, nanoparticles, micelles, microparticles, liposomes, a hydrogel or another new formulation.

Additionally, the present invention is not limited to any type of the drug contained in the dispersed substance 40. Typically, the drug acts to inhibit cell proliferation, and may be either a single drug or a combination of more drugs. Further, the drug may be one of an mTOR inhibitor, paclitaxel and its derivatives, antiplatelet agents, cilostazol, ticlopidine, triptolide, dexamethasone, methotrexate, fluorouracil, mercaptopurine, hydroxyurea, cytarabine, carboplatin, cisplatin, oxaliplatin, dicycloplatin, daunorubicin, doxorubicin and arsenic trioxide, or a combination thereof. The mTOR inhibitor may be one of rapamycin (sirolimus), everolimus, deforolimus, temsirolimus and zotarolimus, or a combination thereof.

The medical delivery device 20 further includes a push mechanism connected to the first housing member 21. The second storage chamber 24 defines a delivery port (not shown) configured to communicate with the balloon catheter 10, which is considered as an external mechanism herein. The external mechanism may be implemented by those of ordinary skill in the art alternatively as a catheter or the like. During use, the medical delivery device 20 can be configured in different operational configurations including a first operational configuration, a second operational configuration and a third operational configuration. In the first operational configuration of the medical delivery device 20, the first storage chamber 23 and the second storage chamber 24 are isolated from each other without mutual communication and configured for separate storage of the liquid dispersion medium 30 and the dispersed substance 40. In the second operational configuration of the medical delivery device 20, the first storage chamber 23 and the second storage chamber 24 are brought into communication with each other so that the liquid dispersion medium 30 can enter the second storage chamber 24 and mix with the dispersed substance 40 to produce a dispersion system. Preferably, uniform dispersion is achieved by ultrasonic agitation. In the third operational configuration of the medical delivery device 20, the push mechanism can drive the first housing member 21 to move relative to the second housing member 22, causing the dispersion system 40 in the second storage chamber 24 to flow through the delivery port in the second storage chamber 24 into the balloon catheter 10.

It would be appreciated that, after the first storage chamber 23 is brought into communication with the second storage chamber 24, it is preferred that the push mechanism applies a pressure, which causes the liquid dispersion medium 30 in the first storage chamber 23 to enter the second storage chamber 24. With this configuration, the liquid dispersion medium 30 can be fully mixed with the dispersed substance 40 in a desirable way, before the dispersion system moves into the balloon catheter 10 as a result of the pressurization by the push mechanism. After that, the dispersion system travels through the catheter body 11 and reaches the balloon 12. It then flows out of the balloon 12 through the micropores therein and is absorbed by target tissue.

Thus, the drug delivery system according to embodiments of the present invention combines the preparation, storage and delivery of a dispersion system. Compared with the prior art, the needs for an additional external chamber for storage of a drug preparation and for external fluidization of the drug preparation and transfer of the prepared fluid into a dilator are dispensed with, reducing transfers of the dispersion system. This can not only reduce the complexity of clinical surgery, but can also lower the risk of the dispersion system being contaminated during delivery, resulting in increased surgical safety.

Preferably, the push mechanism includes a handle 25, a plunger 26 and a pushrod 27. The handle 25 is connected to the first housing member 21 and protrudes out of the second housing member 22. The handle 25 may be integral with the first housing member 21, or provided separately therefrom. The plunger 26 is disposed within the first housing member 21. The pushrod 27 is inserted through the handle 25 and connected to the plunger 26. The first storage chamber 23 is situated between the plunger 26 and the second storage chamber 24. The pushrod 27 is configured to be selectively locked to the handle 25. When the pushrod 27 is unlocked from the handle 25 and when the first storage chamber 23 is in communication with the second storage chamber 24, the pushrod 27 can be used to move the plunger 26 to urge the liquid dispersion medium 30 into the second storage chamber 24, where it is mixed with the dispersed substance 40 to produce the dispersion system. When the pushrod 27 is locked to the handle 25, both the pushrod 27 and the handle 25 may be manipulated to move the first housing member 21, thereby causing the dispersion system in the second storage chamber 24 to flow through the delivery port into the balloon catheter 10. With this configuration, the first housing member 21 that defines the first storage chamber 23 can additionally serve as the plunger, resulting in a simpler structure which can be operated in a labor-saving and convenient manner. Moreover, full mixing of the liquid dispersion medium 30 with the dispersed substance 40 can be facilitated, and a desirable mixing result can be obtained.

Preferably, the medical delivery device 20 further includes a locking mechanism for selectively locking the pushrod 27 to the handle 25 so that the pushrod 27 is kept stationary relative to the handle 25 during delivery of the dispersion system, ensuring reliable delivery. Accordingly, the pushrod 27 may be unlocked from the handle 25, before the plunger 26 is moved. After being released, the pushrod 27 may be manipulated to push the plunger 26 to move relative to the first housing member 21. Moreover, after the dispersion system is prepared, the pushrod 27 may be relocked to the handle 25, and they may be then both used to move the first housing member 21 relative to the second housing member 22 to force the dispersion system to flow into the balloon catheter 10. In other embodiments, the locking mechanism may be omitted, and the pushrod 27 and the handle 25 may be instead maintained stationary relative to each other manually. The locking mechanism may include a locking recess and a locking projection, one of which is provided on the pushrod 27, and the other is on the handle 25.

Figure 2:
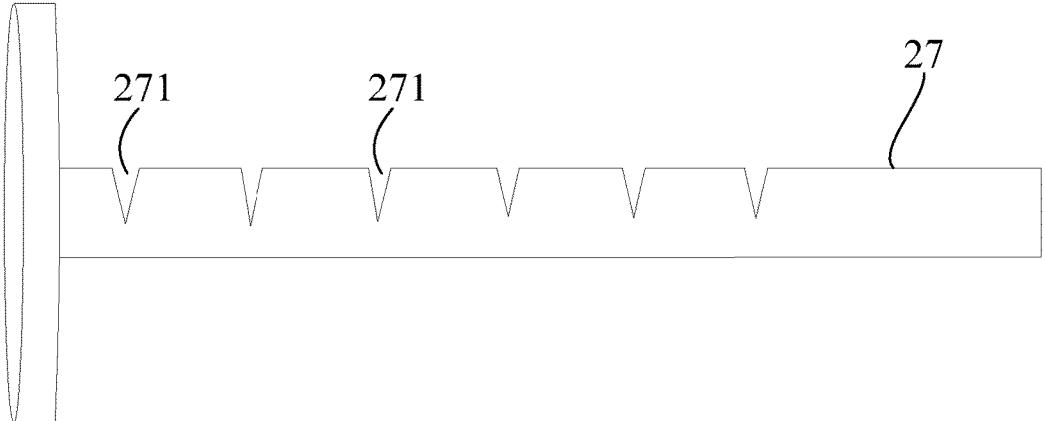
FIG. 2 is a schematic diagram showing the structure of a pushrod according to a preferred embodiment of the present invention, which is provided with a plurality of locking recesses along its lengthwise direction.
Figure 3:
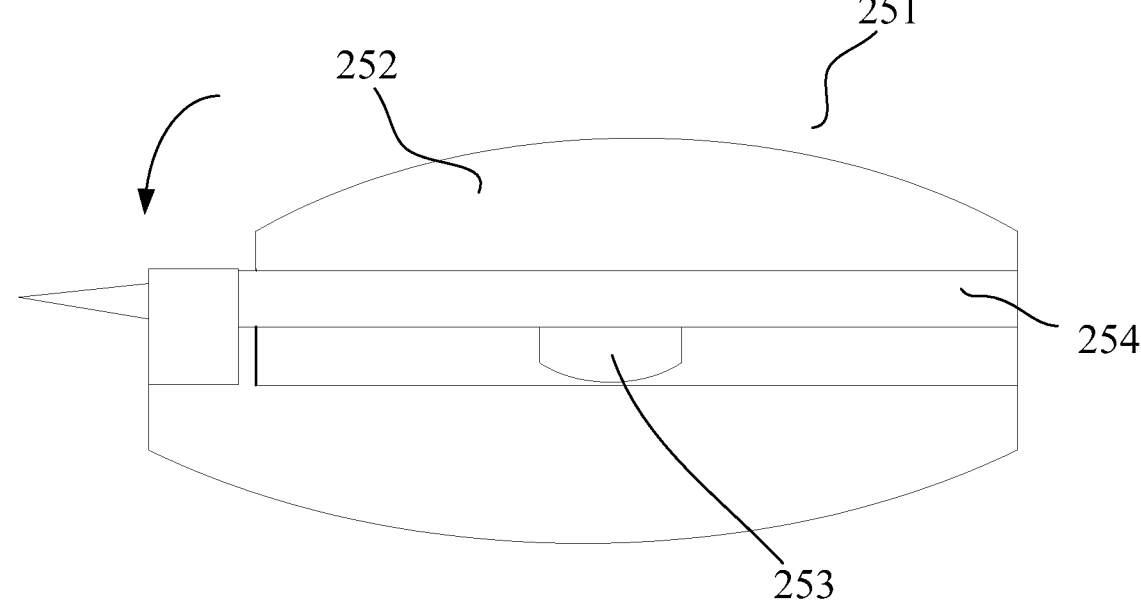
FIG. 3 is a schematic diagram showing the structure of a locking box in a locking mechanism according to a preferred embodiment of the present invention.
Figures 4, 5:
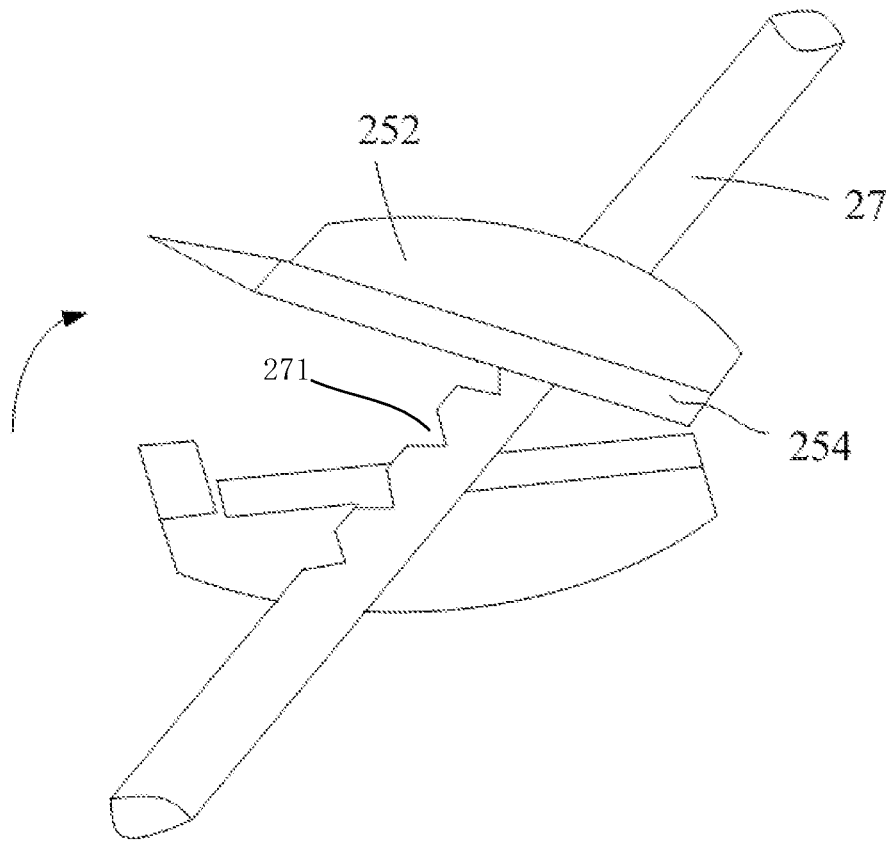
FIG. 4 is a schematic diagram showing how a locking box interacts with a pushrod in a locking mechanism according to a preferred embodiment of the present invention, in which the pushrod is unlocked.
FIG. 5 is a schematic diagram showing locking posts provided on a raised portion defined by a proximal end portion of a handle according to a preferred embodiment of the present invention.

Optionally, as shown in FIGS. 2 to 4, in the present embodiment, one or more first locking recesses 271 may be provided on the pushrod 27. Preferably, a plurality of first locking recesses 271 are spaced apart in a lengthwise direction of the pushrod 27. This allows a more flexible locking approach in which locking can be accomplished at multiple locations. Moreover, the first locking projection 251 may be provided on the handle 25. Additionally, a proximal end portion of the handle 25 may define the first locking projection 251 in the form of a locking box 252. Accordingly, as shown in FIG. 3, the locking mechanism may further include the locking box 252, which is openable and closable and defines a slot 253 allowing passage of the pushrod 27 therethrough. The locking box 252 may have a bolt 254 configured to selectively engage with any one of the first locking recesses 271 on the pushrod 27. As shown in FIG. 4, when the locking box 252 is opened in the direction indicated by the arrow, the pushrod 27 is unlocked and become movable. On the contrary, as shown in FIG. 3, when the locking box 252 is closed in the direction indicated by the arrow, the bolt 254 resting in one of the first locking recesses 271 on the pushrod 27 is fastened, making the pushrod 27 unable to move.

Figure 6:
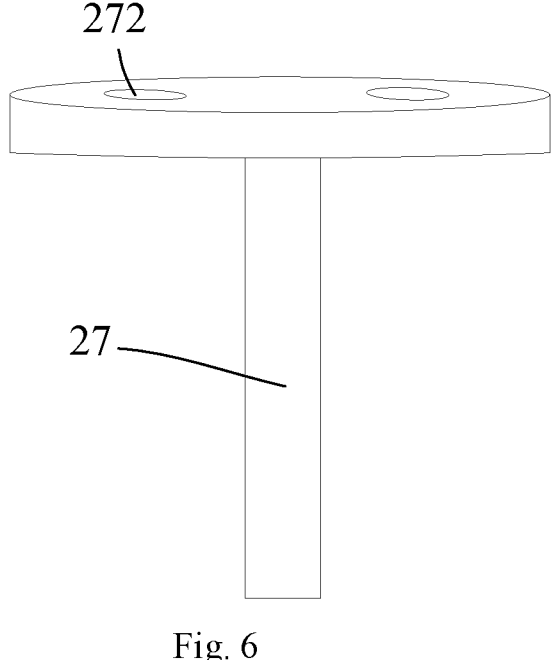
FIG. 6 is a schematic diagram showing how locking recesses in a pushrod interact with locking posts according to a preferred embodiment of the present invention.
Figure 7:
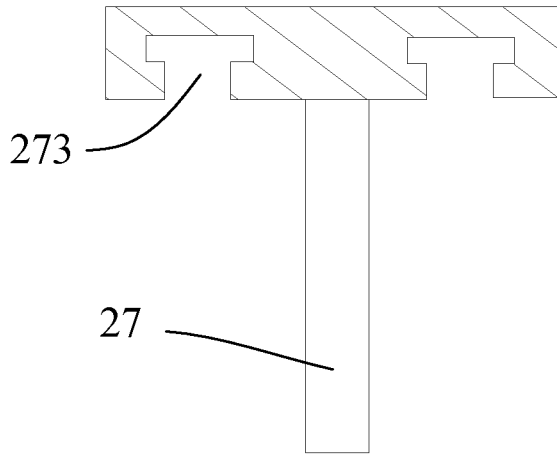
FIG. 7 is an axial cross-sectional view showing how locking recesses in a pushrod interact with locking posts according to another preferred embodiment of the present invention.

In other embodiments, as shown in FIG. 5, locking posts 255 may be provided on the proximal end portion of the handle 25 as second locking projections. Generally, two locking posts 255 are provided in symmetry. Additionally, the proximal end portion of the handle 25 may define a raised portion 256, and the locking posts 255 may be provided on the raised portion 256. As shown in FIG. 6, locking slots 272 may be provided in the pushrod 27 as second locking recesses, which can engage and cooperate with the locking posts 255. The locking slots 272 may be through holes. Alternatively, as shown in FIG. 7, third locking recesses 273 complementary in shape to the locking posts 255 may be defined in the pushrod 27. In this case, when the pushrod 27 is pushed to a limit position, the locking posts 255 on the proximal end portion of the handle 25 may come into engagement and cooperation with the third locking recesses 273, locking the pushrod 27.

It would be appreciated that the foregoing locking approaches are merely examples and should not be construed as limiting the present invention in terms of the structure of the locking mechanism. Moreover, it is possible to either provide only the locking box 252 or the locking posts 255, or provide both of them. It would be also appreciated that the raised portion 256 of FIG. 5 defines a central bore allowing insertion of the pushrod 27 therethrough (not shown). Further, the raised portion and the locking slots may be interchanged in position.

The present invention is not particularly limited to how the first storage chamber 23 and the second storage chamber 24 are brought into communication. In some embodiments, this may be accomplished with a radio controlled valve. For example, as shown in FIG. 1, a spacer 28 may be provided between the first storage chamber 23 and the second storage chamber 24, and the radio controlled valve may be provided on the spacer 28. The radio controlled valve may be opened or closed to bring the two storage chambers into mutual communication or separate them apart. The first storage chamber 23 and second storage chamber 24 may come into communication with each other when the radio controlled valve is opened. In some embodiments, the spacer 28 may be designed with a weak area having a pressure resistance limit lower than that of the reset of the spacer 28. In this case, the weak area will be first broken under the action of pressure acting on the spacer 28, bringing the two storage chambers into communication with each other. In some embodiments, the spacer 28 may be configured as an easily pierceable thin film (i.e., a film structure), such as an aluminum foil or a thin film made of polyvinyl chloride, polyethylene, polypropylene, polystyrene or another resin. Additionally, the thin film is preferably made of a water-proof material.

In this embodiment, the spacer 28 is configured as an easily pierceable structure, which is simple in structure and easy to implement. As shown in FIG. 1, the spacer 28 and the first housing member 21 together delimit the first storage chamber 23, while the spacer 28 and a piercing mechanism 29 together delimit a nozzle chamber (not labeled). The piercing mechanism 29 is positioned between the spacer 28 and the second storage chamber 24 and configured to tear the spacer 28. Specifically, the piercing mechanism 29 may include a base and piercing elements arranged on the base. The base may be mounted on an inner wall surface of the second housing member 22, and the piercing elements may be provided on a side of the base facing toward the spacer 28. As a result of the handle 25 being moved toward the piercing mechanism 29, the first storage chamber 23 will be driven to move toward the piercing mechanism 29. The piercing mechanism 29 can make the spacer 28 not hermetic any longer. The piercing mechanism 29 may define channels for passage of the liquid dispersion medium 30 therethrough so that when the spacer 28 is torn open, the liquid dispersion medium 30 can flow out of the first storage chamber 23 through the piercing mechanism 29.

Figure 8:
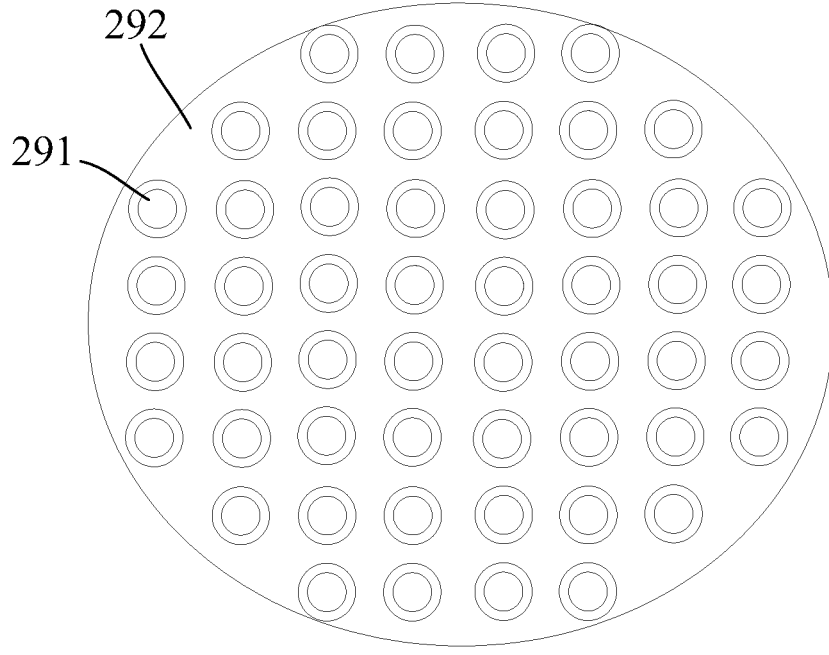
FIG. 8 is a top view of a piercing mechanism according to a preferred embodiment of the present invention, which includes a solid baseplate and bored needle.
Figure 9:
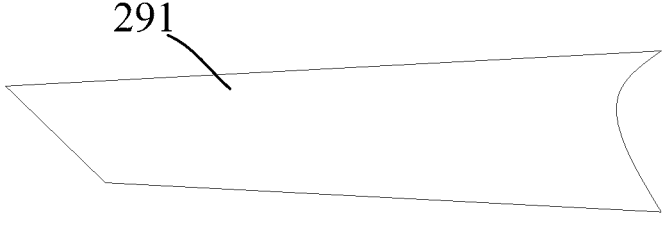
FIG. 9 is a schematic diagram showing the structure of a portion of a bored needle according to a preferred embodiment of the present invention.

In an optional embodiment, as shown in FIGS. 8 and 9, in conjunction with FIG. 1, the piercing mechanism 29 may include a baseplate 292 and one or more bored needles 291 arranged on the baseplate 292. The baseplate 292 may be a solid plate serving as the base, and the bored needles 291 may act as the piercing elements. The bored needles 291 may define respective bores which axially extend through both the needles and the baseplate 292. With this design, after the spacer 28 is torn open, the liquid dispersion medium 30 can pass through the piercing mechanism 29. Further, in case of a plurality of bored needles 291, these bored needles 291 are preferably evenly distributed over the baseplate 292, but the present invention is not limited to any particular distribution pattern. Each bored needle 291 may have a diameter of 50 microns to 1000 microns, preferably 20 microns to 200 microns. In case of a single bored needle 291, it may have a greater diameter such as 0.5 millimeters to 500 millimeters, preferably 0.5 millimeters to 10 millimeters. The present invention is not limited any particular shape or size of the bored needles 291, as long as they can effectively pierce the spacer 28.

With reference to FIG. 1, in a preferred operating mode, the handle 25 may be pushed toward a distal end of the drug delivery system, causing the spacer 28 to move toward the bored needles 291. Additionally, after the spacer 28 is pierced by the bored needles 291, the plunger 26 may be manipulated to urge the liquid dispersion medium 30 to flow out of the first storage chamber 23 into the second storage chamber 24 to dissolve the dispersed substance 40. After that, the pushrod 27 may be further pushed to expel the air in the system, and upon reaching a proper location relative to the locking projection on the first housing member 21, it can be fixed to the first housing member 21.

Figure 10:
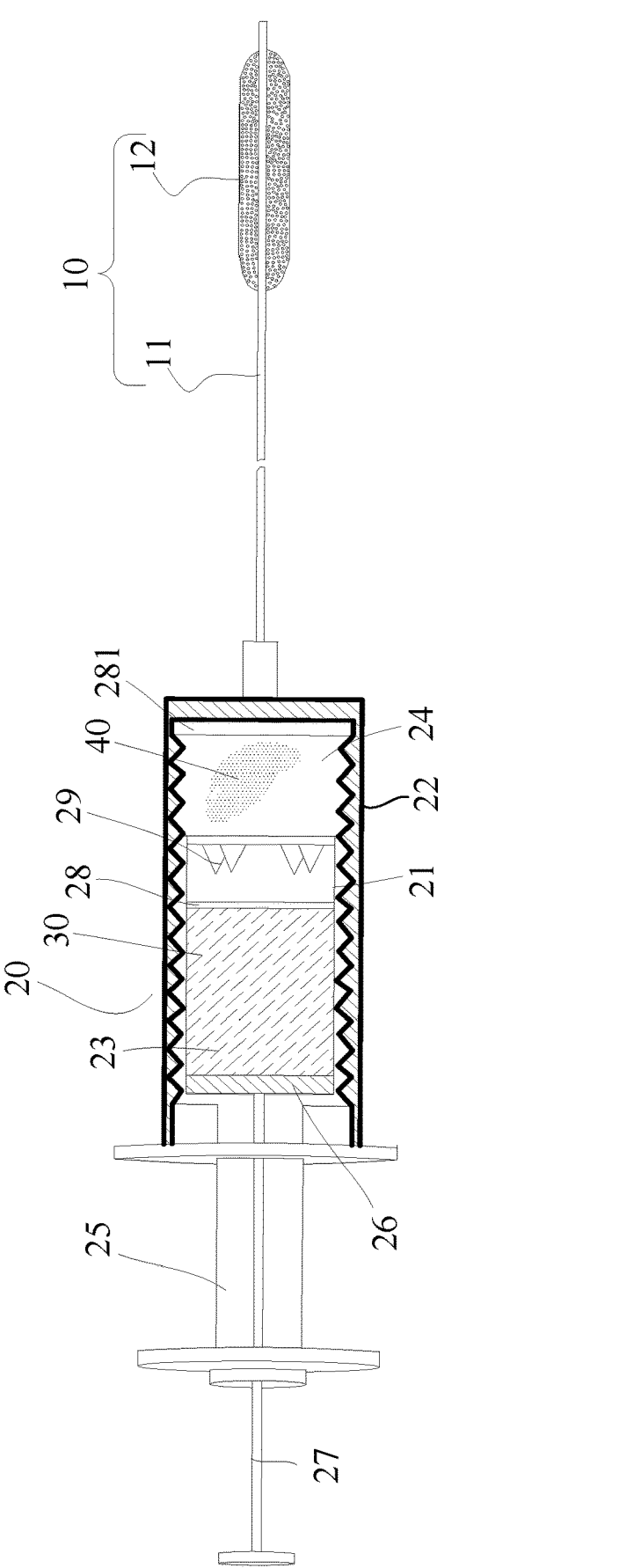
FIG. 10 is a schematic diagram showing the structure of a drug delivery system according to another preferred embodiment of the present invention, in which a piercing mechanism includes blades.
Figure 11:
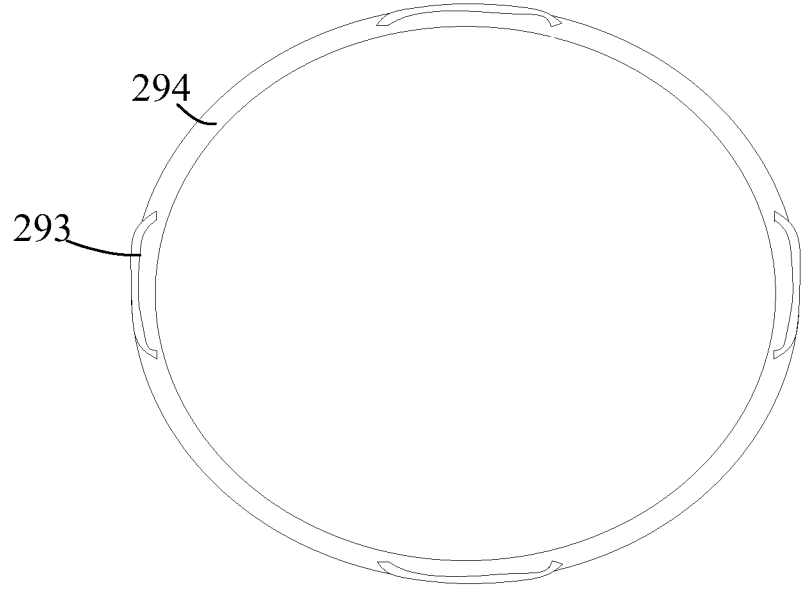
FIG. 11 is a top view of a piercing mechanism according to a preferred embodiment of the present invention, which includes a ring and a plurality of blades arranged on the ring.
Figure 12:
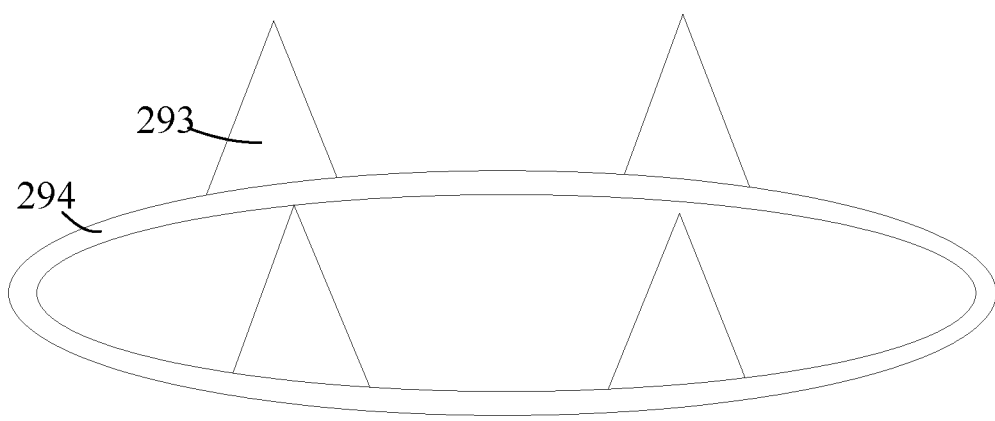
FIG. 12 is a perspective view of a piercing mechanism according to a preferred embodiment of the present invention, which includes a ring and a plurality of blades arranged on the ring.
Figure 13:
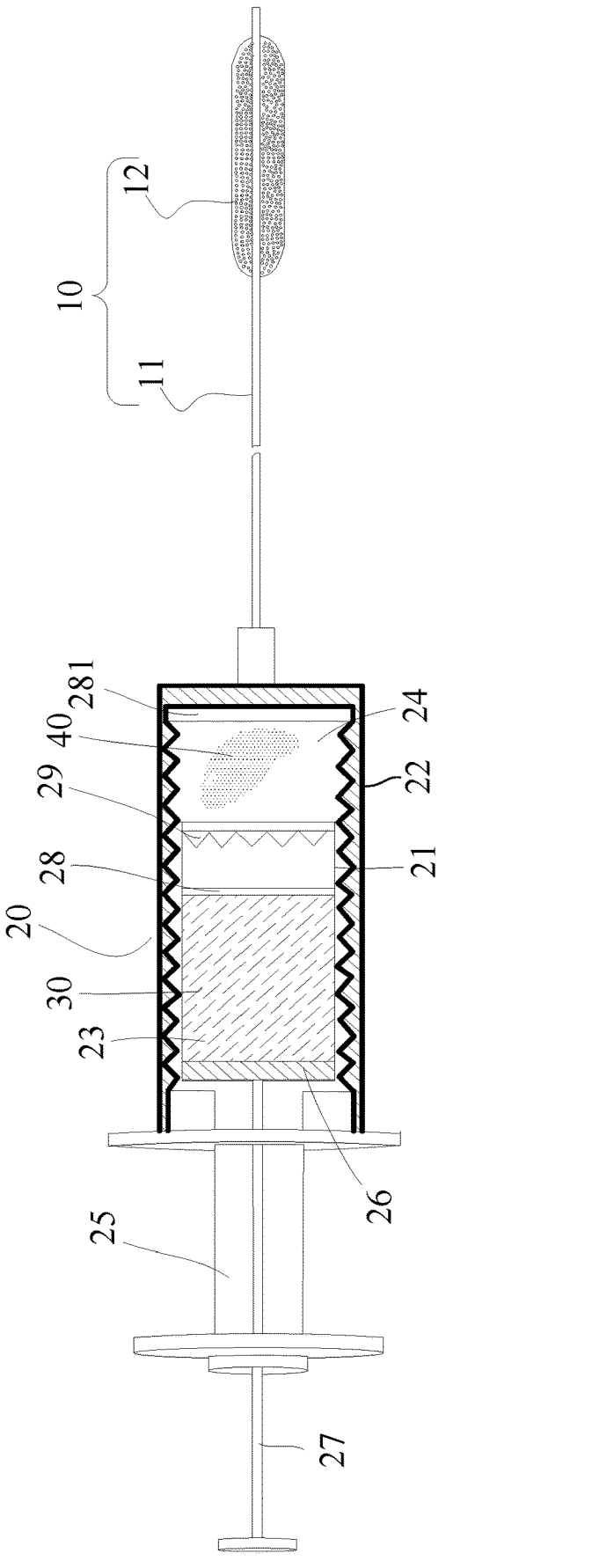
FIG. 13 is a schematic diagram showing the structure of a drug delivery system according to a further preferred embodiment of the present invention, in which a piercing mechanism includes sawtooth bars.
Figure 14:
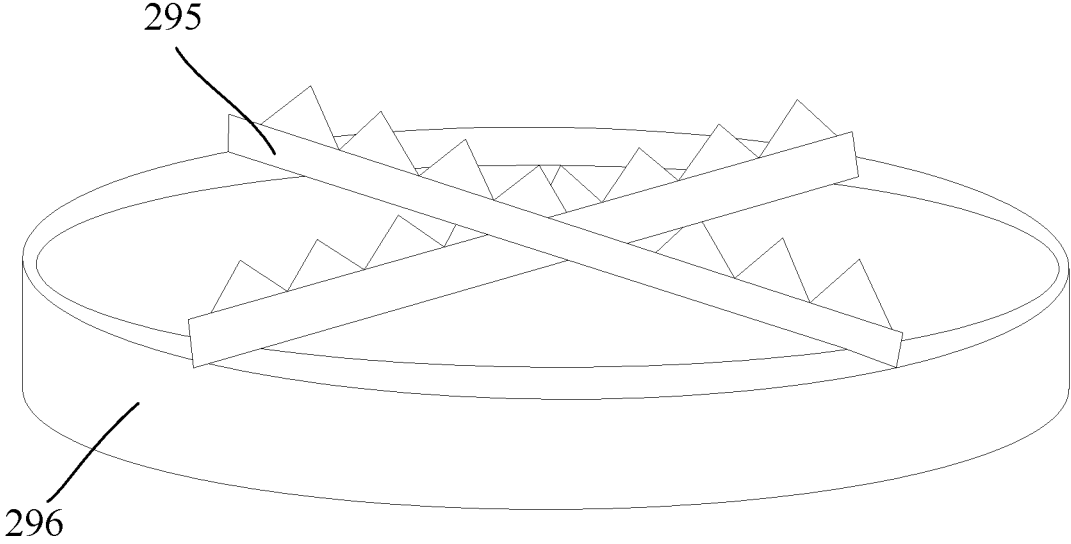
FIG. 14 is a perspective view of a piercing mechanism according to a preferred embodiment of the present invention, which includes a ring and two sawtooth bars arranged on the ring.

As shown in FIGS. 10 to 12, in other embodiments, the piercing mechanism 29 and the first housing member 21 may together define an accommodating chamber, which is divided into the first storage chamber 23 and the nozzle chamber by the spacer 28. In this embodiment, the spacer 28 is configured as an elastic, easily pierceable thin film. In a preferred operating mode, the plunger 26 may be pushed toward the distal end of the drug delivery system until the spacer 28 comes into contact with the bored needles 291, or is pierced by a blade 293. Here, it would be appreciated that, during advancement of the plunger 26 toward said distal end, the spacer 28 is fixed at both ends to the first housing member 21. However, as the spacer 28 is a thin film, it can easily deform under the effect of a pressure and thereby come into contact with the bored needles 291. In this embodiment, the piercing mechanism 29 may include the blade 293 and a ring 294. One or more blades 293 may be provided, and the number of them may be, but is not limited to, four. The plurality of blades 293 are preferred to be uniformly arranged on the ring 294 along a circumference thereof. In this case, the ring 294 serves as the base, and the blades 293 as the piercing elements. Moreover, the ring 294 may define a lumen allowing passage of the liquid dispersion medium 30 therethrough. Alternatively, as shown in FIGS. 13 to 14, the piercing mechanism 29 may include sawtooth bars 295 and an annular base 296, wherein the sawtooth bars 295 are each fixed at both ends to the annular base 296. In this case, the annular base 296 serves as the aforementioned base, and the sawtooth bars 295 as the piercing elements. Likewise, the annular base 296 may define a lumen allowing passage of the liquid dispersion medium 30 therethrough. Preferably, a plurality of sawtooth bars 295 is provided. For example, two crossed or parallel sawtooth bars 295 may be provided on the annular base 296.

Preferably, the second housing member 22 has an internal thread, and the first housing member 21 has an external thread engageable with the internal thread. In this case, the dispersion system can be pressurized and injected as a result of threaded rotation of the first housing member 21, and a flow rate of the dispersion system can be controlled through adjusting a speed of the rotation.

The medical delivery device 20 may further include a monitoring mechanism (not shown) for monitoring the pressure and/or flow rate of the dispersion system. The medical delivery device 20 may further include a display device for displaying the pressure and/or flow rate of the dispersion system thereon. The pressure monitoring may be accomplished with a pressure sensor, and the flow rate monitoring with a flow rate sensor. However, the present invention is not limited to any particular implementation in this regard.

Further, as shown in FIGS. 1, 10 and 13, the medical delivery device 20 is preferred to further include a filtration membrane 281 disposed within the second storage chamber 24 so as to cover the delivery port. More preferably, pores in the filtration membrane 281 have a diameter smaller than the size of the dispersed substance 40. In this way, large particles therein that may cause clogging of the balloon catheter 10 can be filtered out. The diameter of the pores in the filtration membrane 281 is preferably 0.1 micron to 100 microns, more preferably 0.1 micron to 40 microns, even more preferably 0.1 micron to 10 microns. Additionally, a valve for bringing the balloon catheter 10 into communication with the medical delivery device 20 or separating them apart may be provided at the proximal end of the balloon catheter 10. It is to be noted that the second housing member 22 is outlined partially with bolded lines in FIGS. 1, 10 and 13 to more clearly illustrate the positioning of the first housing member 21 and the second housing member 22.

The present invention is not limited to any particular method of manufacturing the drug delivery system. For example, in an optional manufacturing method, the balloon catheter 10 is first formed, and the formation may include forming a balloon 12 with pores. This may be accomplished by, for example, vertically perforating a semi-compliant angioplasty balloon with Hamilton microliter syringe needles and thereby forming micropores therein. The medical delivery device 20 may be then formed. A lyoprotectant (e.g., trehalose) may be added to the drug fluid to be infused, which has been prepared in advance, and the drug fluid may be then freeze-dried into the dispersed substance 40 in the form of a powder, tablets, capsules or the like. The dispersed substance 40 in the lyophilized form may be loaded in the second storage chamber 24, and the liquid dispersion medium 30 (e.g., a saline solution) may be pre-loaded in the first storage chamber 23 that is separate from the external nozzle chamber. After that, the balloon catheter 10 may be connected to the proximal end of the medical delivery device 20.

The foregoing description presents merely preferred embodiments of the present invention and is not intended to limit the scope of the present invention in any way. Any and all changes and modifications made by those of ordinary skill in the art in light of the above teachings without departing from the spirit of the present invention are intended to be embraced in the scope as defined by the appended claims.

The invention claimed is:

1. A medical delivery device, comprising:

a housing comprising a first housing member and a second housing member, the first housing member defining a first storage chamber for storing a liquid dispersion medium therein, the second housing member disposed over the first housing member, the second housing member defining a second storage chamber for storing a dispersed substance therein, the second storage chamber having a delivery port for communicating with an external mechanism; and a push mechanism connected to the first housing member, wherein the medical delivery device has a first operational configuration, a second operational configuration and a third operational configuration, wherein in the first operational configuration of the medical delivery device, the first storage chamber is not in communication with the second storage chamber;

in the second operational configuration of the medical delivery device, the first storage chamber is in communication with the second storage chamber, allowing the liquid dispersion medium to enter the second storage chamber to be mixed with the dispersed substance to produce a dispersion system; and in the third operational configuration of the medical delivery device, the push mechanism drives the first housing member to move relative to the second housing member, causing the dispersion system in the second storage chamber to flow through the delivery port into the external mechanism;

wherein the push mechanism comprises a handle, a plunger and a pushrod, the handle connected to the first housing member and protruding out of the second housing member, the plunger disposed in the first housing member, the pushrod passed through the handle and connected to the plunger, wherein the first storage chamber is positioned between the plunger and the second storage chamber;

the pushrod is configured to be selectively locked to the handle;

when the pushrod is unlocked from the handle, and when the first storage chamber is brought into communication with the second storage chamber, the pushrod drives the plunger to move, causing the liquid dispersion medium to enter the second storage chamber and be mixed with the dispersed substance to produce the dispersion system; and when the pushrod is locked to the handle, the pushrod and the handle together drive the first housing member to move, causing the dispersion system in the second storage chamber to flow through the delivery port into the external mechanism;

a locking mechanism for selectively locking the pushrod to the handle;

wherein the locking mechanism comprises a locking projection and a locking recess, one of which is provided on the pushrod, and the other is provided on the handle.

2. The medical delivery device of claim 1, wherein the locking recess is provided on the pushrod, and the locking projection is provided on the handle, wherein the locking mechanism further comprises an openable and closable locking box serving as the locking projection, the locking box defined at a proximal end of the handle and comprising a slot and a bolt, wherein a plurality of locking recesses are spaced apart along a lengthwise direction of the pushrod; the pushrod is inserted in the slot; and the bolt is configured to be selectively locked in any one of the locking recesses on the pushrod; and/or wherein the handle defines a raised portion at the proximal end thereof, the raised portion is provided thereon with a locking post serving as the locking projection, and a locking recess is provided at a proximal end of the pushrod and configured to engage and cooperate with the locking post.

3. The medical delivery device of claim 1, wherein the second housing member has an internal thread, and the first housing member has an external thread engageable with the internal thread.

4. The medical delivery device of claim 1, wherein a spacer is disposed between the first storage chamber and the second storage chamber, the spacer is configured to be torn under an action of a force, and the first storage chamber comes into communication with the second storage chamber when the space is torn.

5. The medical delivery device of claim 4, wherein the spacer is configured as a film structure which is configured to be torn under the action of a force, wherein the medical delivery device further comprises a piercing mechanism disposed between the spacer and the second storage chamber and configured to tear the film structure.

6. The medical delivery device of claim 5, wherein the piercing mechanism comprises a base and a piercing element arranged on the base, the base connected to the second housing member, the piercing element arranged on a side of the base facing the spacer, the piercing mechanism defining a channel allowing passage of the liquid dispersion medium therethrough, wherein the spacer defines the first storage chamber together with the first housing member and defines a nozzle chamber together with the piercing mechanism, or wherein the piercing mechanism and the first housing member together defines an accommodating chamber divided by the spacer into the first storage chamber and a nozzle chamber.

7. The medical delivery device of claim 6, wherein the base is a solid baseplate, and the piercing element is a bored needle, or wherein the base is a ring, and the piercing element is made up of a number of blades arranged on the ring along a circumference thereof, or wherein the base is an annular base, and the piercing element is a sawtooth bar which is connected at both ends to the annular base.

8. The medical delivery device of claim 1, further comprising a filtration membrane that is disposed in the second storage chamber and covers the delivery port.

9. The medical delivery device of claim 1, further comprising a monitoring mechanism for monitoring a pressure and/or a flow rate of the dispersion system.

10. A drug delivery system, comprising:

the medical delivery device of claim 1;

a solid dispersed substance arranged in the second storage chamber;

a liquid dispersion medium arranged in the first storage chamber; and a balloon catheter comprising a catheter body and a balloon, the balloon disposed at a distal end of the catheter body and having micropores, the catheter body brought into communication at a proximal end thereof with the delivery port.

\* \* \* \* \*